US00PP18177P3

(12) United States Plant Patent
Boyle

(10) Patent No.: US PP18,177 P3
(45) Date of Patent: Nov. 6, 2007

(54) CACTACEAE PLANT NAMED 'HARMONY'

(50) Latin Name: *Schlumbergera truncata*
Varietal Denomination: Harmony

(75) Inventor: Thomas H. Boyle, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/198,376

(22) Filed: Aug. 4, 2005

(65) Prior Publication Data

US 2007/0033693 P1 Feb. 8, 2007

(51) Int. Cl.
*A01H 5/00* (2006.01)

(52) U.S. Cl. ..... Plt./372
(58) Field of Classification Search ..... Plt./372
See application file for complete search history.

(56) References Cited

U.S. PATENT DOCUMENTS

PP11,327 P 4/2000 Boyle
6,156,959 A 12/2000 Boyle

OTHER PUBLICATIONS

Karle, Renate and Boyle, Thomas H., "Relationships between Floral Morphology, Breeding Behavior, and Flower Longevity in Easter Cactus", *J. Amer. Soc. Hort. Sci*, 1999, vol. 124(3), pp. 296–300, American Society of Horticultural Science, United States.

Karle, Renate et al., "Polyploidy–included Changes in the Breeding Behavior of *Hatiora×graeseri* (Cacteceae)", *J. Amer. Soc. Hort. Sci.*, 2002, vol. 127(3), pp. 397–403, American Society of Horticultural Science, United States.

Parks, C. and Boyle, Thomas H., "Variation in Ploidy Level, Fertility, and Breeding Behavior in Cultivated *Schlumbergera* (Cactaceae)", *Acta Hort.*, 2003, vol. 623, pp. 341–346, International Society for Horticultural Science, United States.

Boyle, et al., "Occurence and Physiological Breakdown of Self–incompatibility in Easter Cactus", *J. Amer. Soc. Hort. Sci.,* 1994, vol. 119(5), pp. 1060–1067, American Society of Horticultural Science, United States.

Barthlott et al., "Notes towards a Monograph of Rhipsalideae (Cactaceae)", *Bradleva*, 1995, vol. 13, pp. 43–79, British Cactus and Succulent Society, United Kingdom.

*Primary Examiner*—Kent Bell
(74) *Attorney, Agent, or Firm*—Law Offices of James R. Cypher

(57) ABSTRACT

A plant variety of the Cactaceae family, *Schlumbergera truncata,* called 'Harmony' having a deep colored bloom characterized as R.H.S. 46 B (red group). The new variety has a strong resistance to bud abscission, a strong propensity for buds to mature and flower, an erect growth habit, and an ability to grow well in relatively cold temperatures.

8 Drawing Sheets

Latin name of genus and species of plant claimed: The new plant is a species of *Schlumbergera truncata.*

Variety denomination: The new plant's varietal denomination is 'Harmony.'

BACKGROUND OF THE INVENTION

The present invention relates to a new and distinct variety of the Cactaceae family. The new variety is named *Schlumbergera truncata* 'Harmony'. The inventor is Thomas H. Boyle, a citizen of the United States.

Many varieties of *Schlumbergera truncata* tend to bloom in the winter in the Northern Hemisphere. Because of their blooming time, there is a large market for these varieties during the Thanksgiving and Christmas seasons as a decorative plant. In fact, the common name for these plants is Christmas Cactus.

There are many commercially developed varieties of Christmas Cactus. Patented varieties include: ('Lavender Doll' (Cobia, U.S. Plant Pat. No. 3,690); 'Christmas Charm' (Cobia et al., U.S. Plant Pat. No. 4,196); 'Rudolph' (Higaki, U.S. Plant Pat. No. 6,234); 'Dasher' (Higaski, U.S. Plant Pat. No. 7,367); and 'Rudolph II' (Martens, U.S. Plant Pat. No. 10,487).

For many varieties of the species, bud abscission is a problem: a large portion of the initial buds that form on the plant fall off before they reach full maturity. Furthermore, many cultivars possess the further undesirable characteristic that many of the buds that do set on the plant fail to mature and bloom. Preferred cultivars resist bud abscission, as well as produce buds that have a propensity to mature.

The present variety, 'Harmony' was developed in Massachusetts, and is a hybrid obtained by cross pollinating flowers of 'Twilight Tangerine' (U.S. Plant Pat. No. 4,200) with pollen collected from flowers of 'Dark Marie' (a non-patented variety). 'Harmony' is similar to its maternal parent in branching architecture, upright habit, flower size, and flower shape. 'Twilight Tangerine' has light orange flowers and 'Dark Marie' has scarlet red flowers. 'Harmony' differs from both parents in its unique flower color and its tepals which do not reflex fully at maturity, which gives the flowers a wider, more aesthetic look. Phylloclade size for 'Harmony' is intermediate between the two parents. 'Harmony' exhibited excellent resistance to fungal pathogens in multiple pot plant trials conducted in Massachusetts.

'Harmony' resists bud abscission, as well as produces buds that have a propensity to mature. The present variety sets many buds per phylloclade often 2 to 3, many of which reach full maturity and bloom generally 1 to 2.

This present variety is also outstanding for its propensity to grow tall and upright, thus giving it a dense appearance.

The pigmented portions of the flowers of the present variety are quite dark, although portions of the white sepaloid tube are visible when flowers are mature as well as the white basal portions of the blades. The pigmentation in the sepals of the new variety falls in the Red Group, with reference to The Royal Horticultural Society of London's Color Chart.

TABLE 1

Comparison Chart of Flower Pigmentation Color

| | 'Harmony' New Variety | 'Camillia' Unpatented commercial var. |
|---|---|---|
| Mature Flower Pigmentation Color in Tepals | R.H.S. 46B | R.H.S. 74 B (red-purple group) |
| Bud 1 mm in size Color | R.H.S. 74 B (red-purple grp.) | R.H.S. 59 C (red-purple grp.) |
| Medium Sized Bud - Ovary Color | 2 mm tall ovary is R.H.S. 143 C (green group) | 4 mm tall ovary is R.H.S. 144 A (yellow-green group) |
| Medium Sized Bud - Tepal Color | 7 mm tall tepals are R.H.S. 145 D (yellow-green group) with R.H.S. 74 B (red - purple tips) | 6 mm tall tepals are R.H.S. 59 C (red-purple group) |
| Large Bud - Ovary Color | 7 mm tall ovary, portions are R.H.S. 145 A (yellow-green group), and portions are R.H.S. 60A (red - purple group) | 6 mm tall ovary is 144 A (yellow-green group) |
| Large Bud - Tepal Color | 27 mm tall tepals are R.H.S. 45 B (red group) | 21 mm tall tepals are R.H.S. 73 A (red-purple grp.) |
| Color of mature phylloclade | R.H.S. 147 A (yellow-green group) | R.H.S. 137 B (green group) |
| Angle of tube w/respect to ovary | tube is slightly angled, ovary upright/same axis with respect to phylloclade on which it grows | |

| | 'Prancer' | 'Maria' Unpatented commercial var. |
|---|---|---|
| Mature Flower Pigmentation Color in Tepals | R.H.S. 74B (red-purple group) | R.H.S. 45 C |
| Bud 1 mm in size Color | R.H.S. 74 B (red-purple grp.) | R.H.S. 74 B (red-purple grp.) |
| Medium Sized Bud - Ovary Color | 5 mm tall ovary is R.H.S. 145 A (yellow-green group) | 3 mm tall ovary is R.H.S. 146 C (yellow-green group) |
| Medium Sized Bud - Tepal Color | 5 mm tall tepals are R.H.S. 74 D (red-purple grp.) | 6 mm tall tepals are R.H.S. 145 C (yellow-green group) with faintly purple tips |
| Large Bud - Ovary Color | 7 mm tall ovary is 145 A (yellow-green group) | 9 mm tall ovary is 145 B (yellow-green group) |
| Large Bud - Tepal Color | 20 mm tall tepals are R.H.S. 74 B (red-purple grp.) | 22 mm tall tepals are R.H.S. 74 C (red-purple grp.) |

TABLE 1-continued

Comparison Chart of Flower Pigmentation Color

| | |
|---|---|
| Color of mature phylloclade | |
| Angle of tube w/respect to ovary | tube is very angled, almost 90 degrees to ovary, ovary upright/same axis on phyllalce |

The pigmented portion of most of the blades of the sepaloid tepals, the tube laminating tepals, and the tube forming tepals is R.H.S. 46B (red group), while in the remaining portions of the tepals, the pigmentation decreases in intensity.

Because the buds of the new variety have a greater propensity to mature, when grown under the proper conditions, at least one bud and often 2 buds per phylloclade will mature and bloom.

The distinguishing characteristics of the new variety are retained by asexually reproduced, successive generations.

In addition, the new variety also possesses the additional commercially desirable characteristics of:

1. a strong propensity to branch with minimal pruning, resulting in a dense appearance;
2. erect stems, resulting in an upright appearance;

The inventor has asexually reproduced the new variety at a commercial nursery in Half Moon Bay, Calif. through three successive generations by cuttings, and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
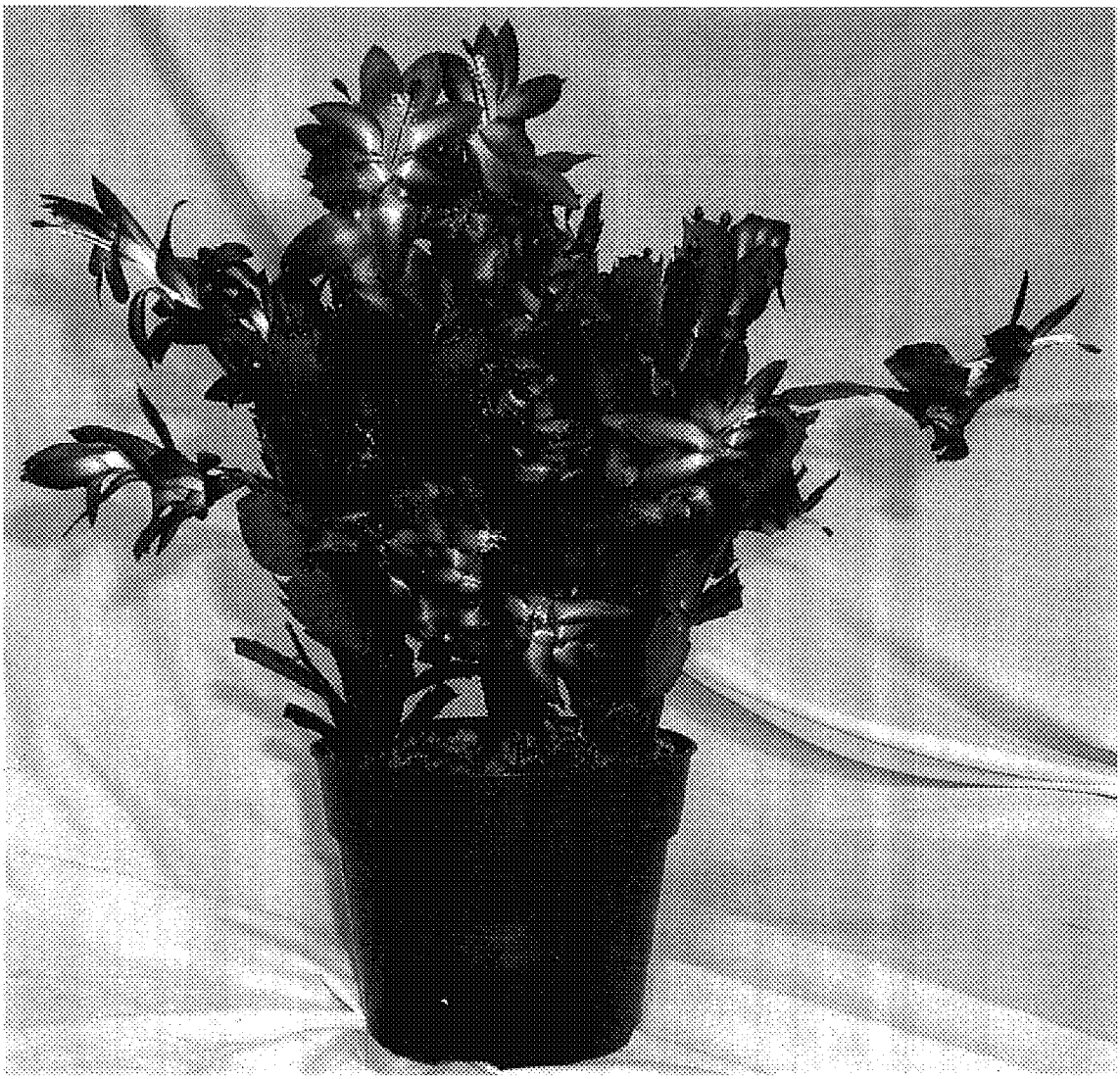
FIG. 1 is a color photograph of a number of plants grown from a number of cuttings in one pot of the new variety illustrating the overall appearance and form of the plant, and the abundance of blooms.
Figure 2:
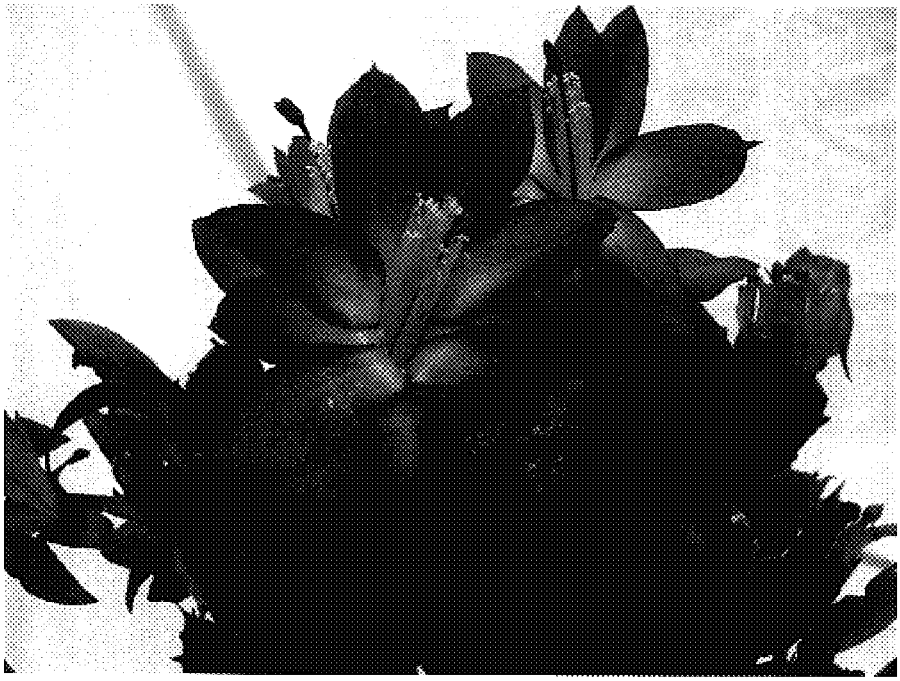
FIG. 2 is a color photograph showing a side view of a fully opened bloom of the new variety on the plant.
Figure 3:
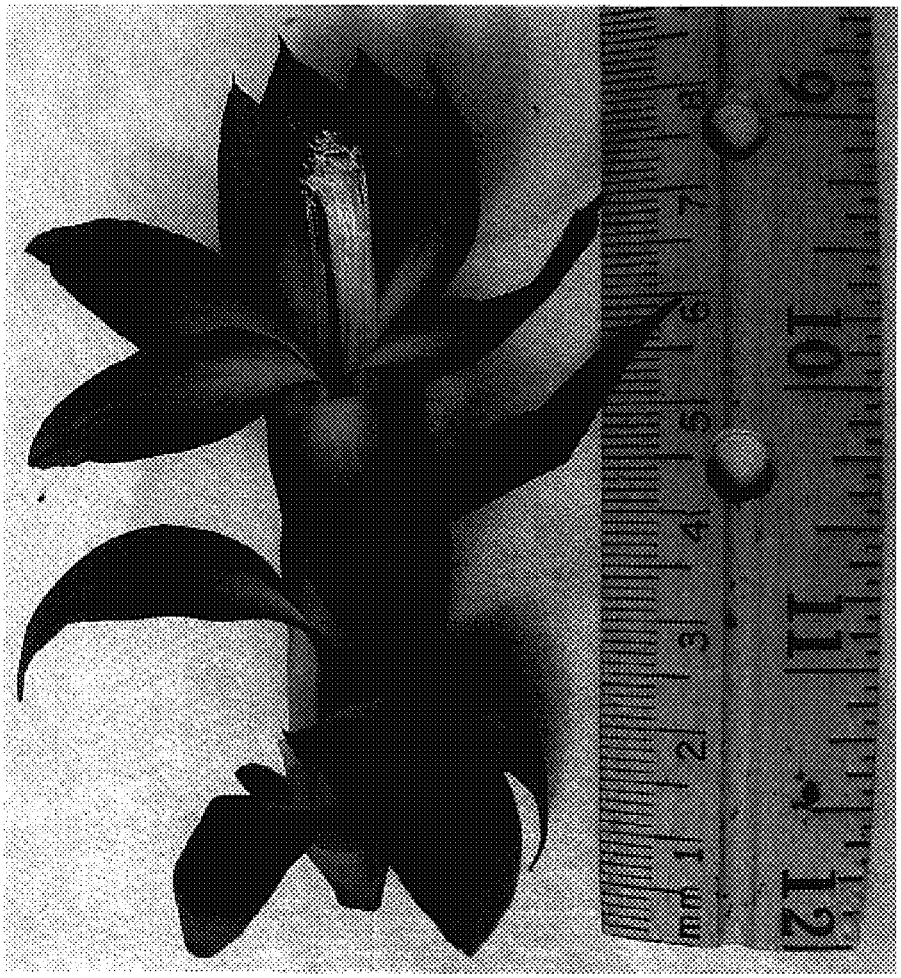
FIG. 3 is a color photograph a fully opened bloom of the new variety.
Figure 4:
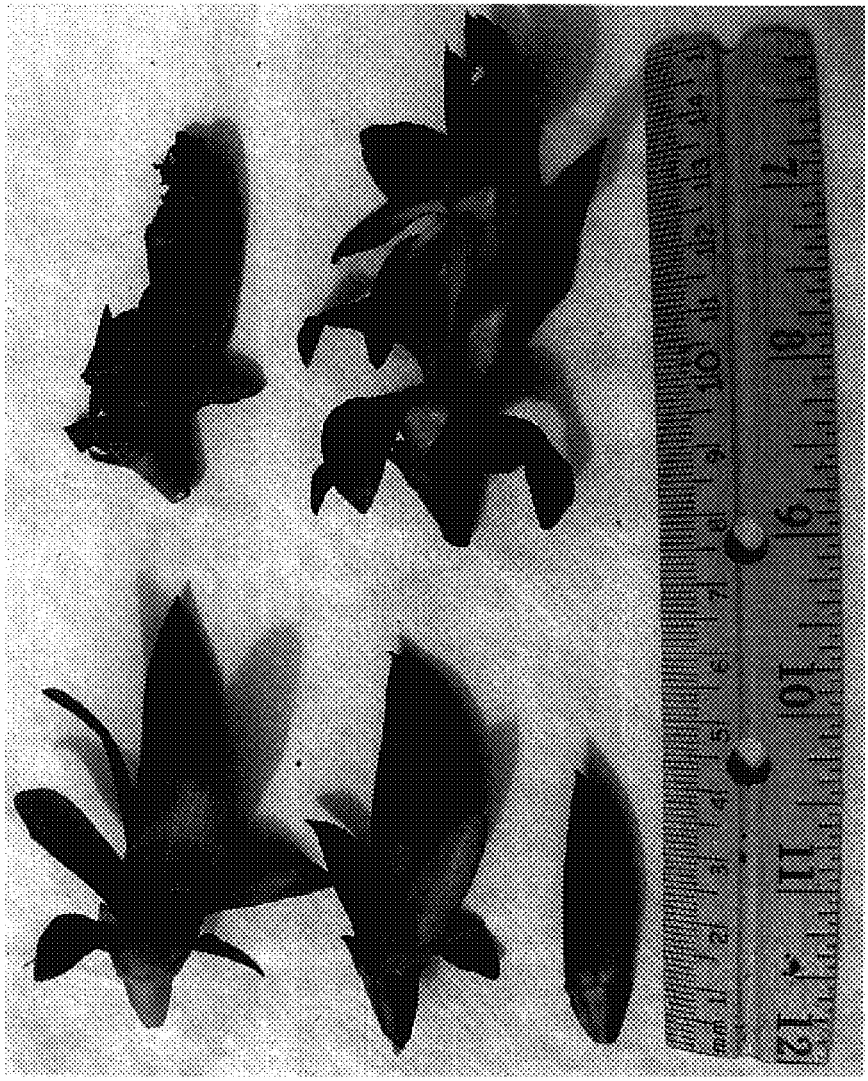
FIG. 4 is a color photograph of blooms in various stages of development removed from a plant of the new variety.
Figure 5:
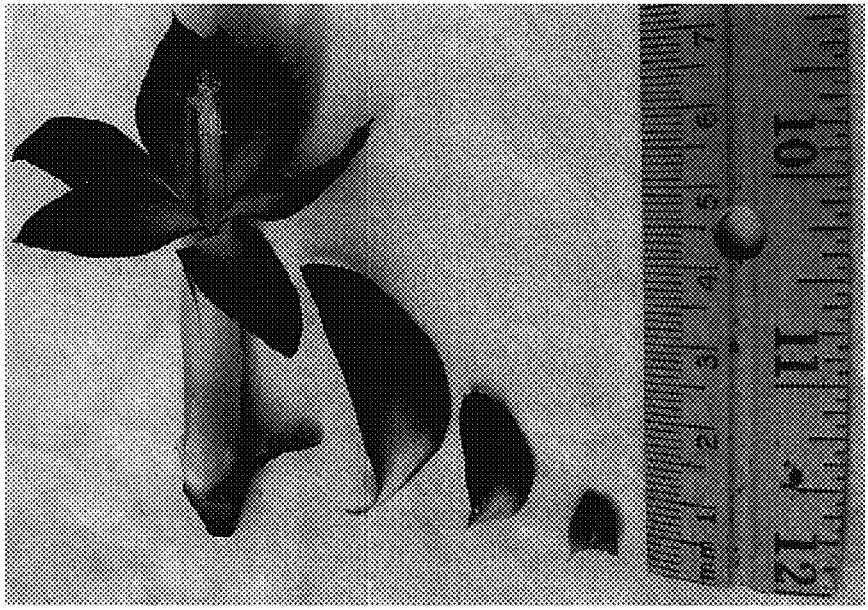
FIG. 5 is a color photograph of a bloom removed from the plant that has had its sepaloid series of tepals removed, some of which are shown next to the bloom.
Figure 6:
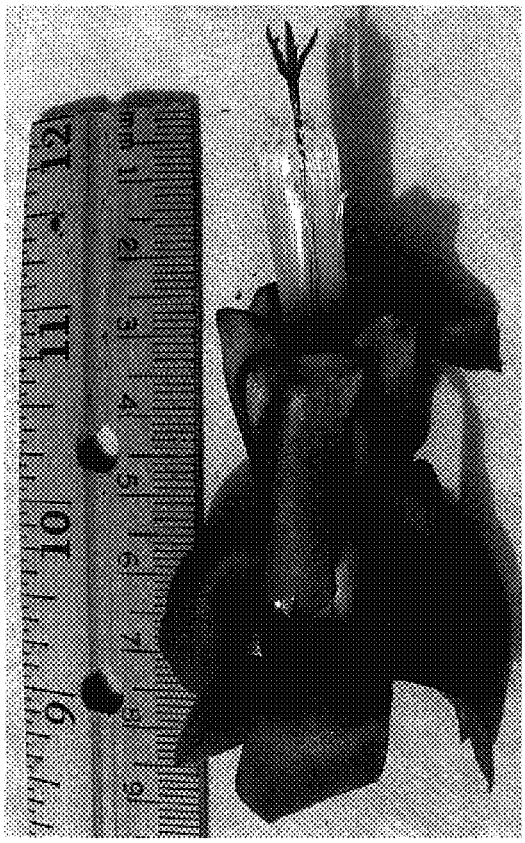
FIG. 6 is a color photograph of a mature bloom removed from the plant, showing the highly reflexed tepals, and exposed stamens and style.
Figure 7:
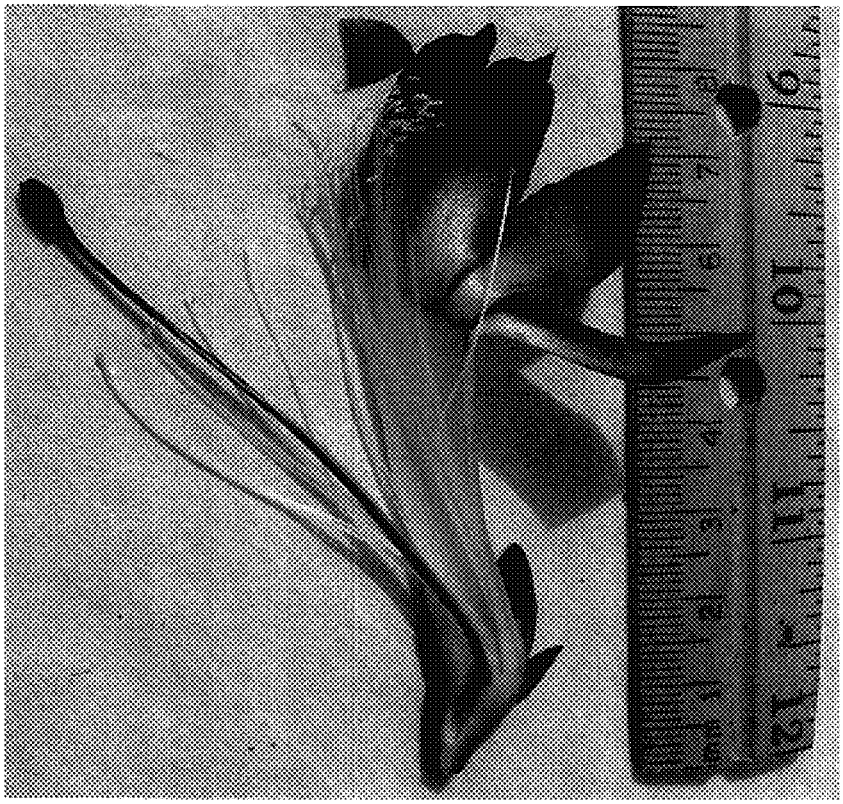
FIG. 7 is a color photograph of a mature bloom removed from the plant that has its outer tepals removed and then sectioned to show the interior of the ovary.
Figure 8:
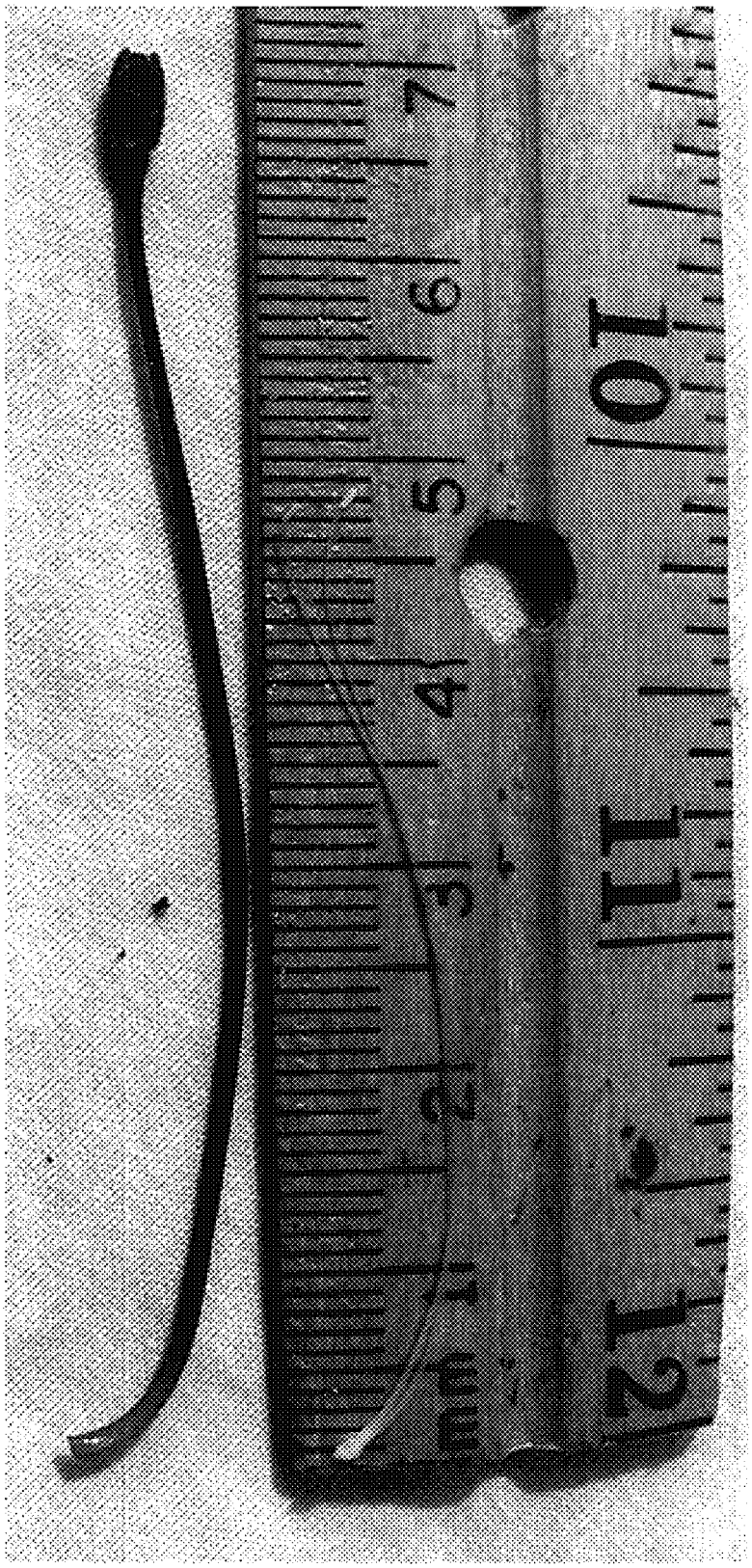
FIG. 8 shows a style and stamens of the present variety removed from the plant.
Figure 9:
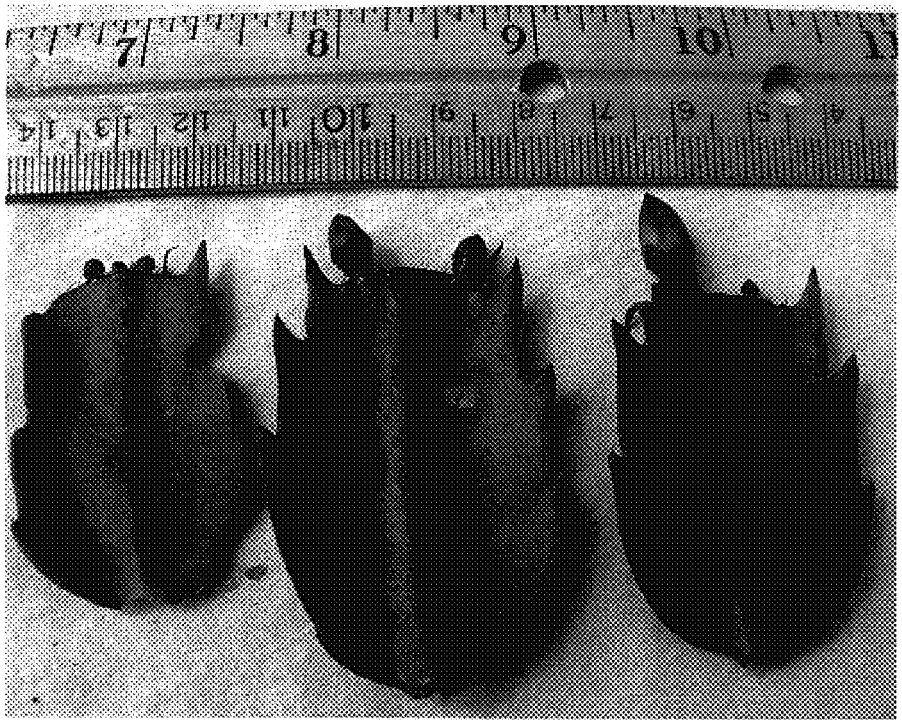
FIG. 9 is a color photograph of three phylloclades removed from the plant, showing buds growing from the apex of the phylloclades.
Figure 10:
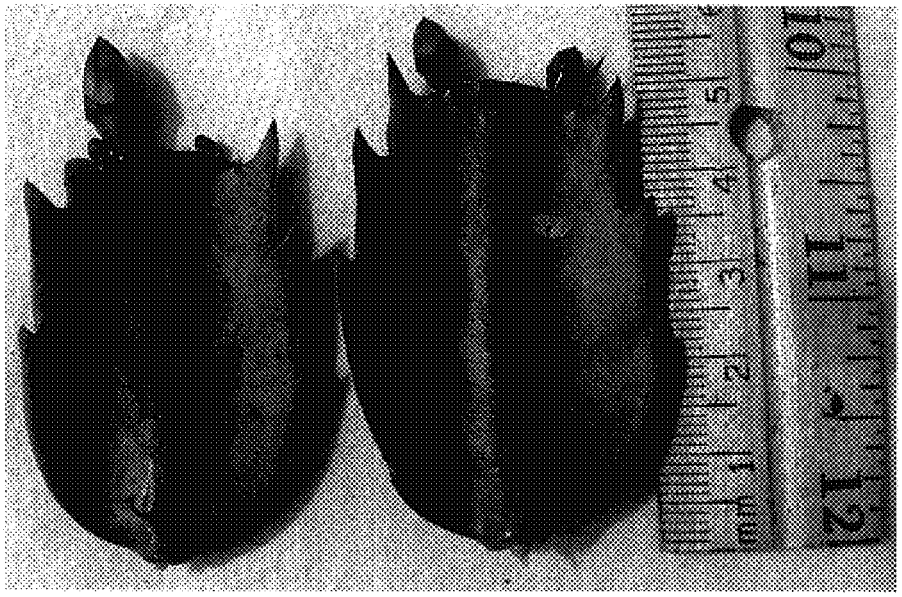
FIG. 10 is a color photograph of two phylloclades removed from the plant, showing buds growing from the apex of the phylloclades.
Figure 11:
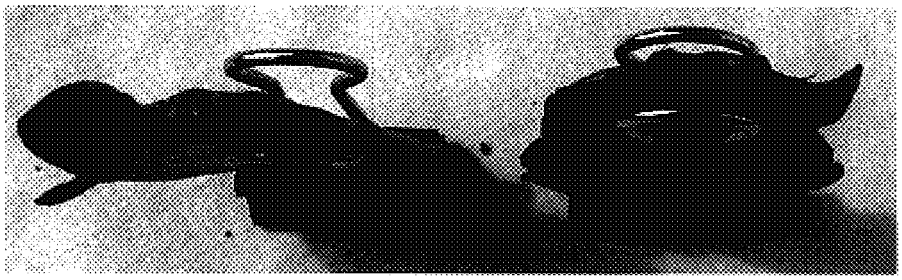
FIG. 11 is color photograph of two phylloclades, looking down on the apexes of the phylloclades.
Figure 12:
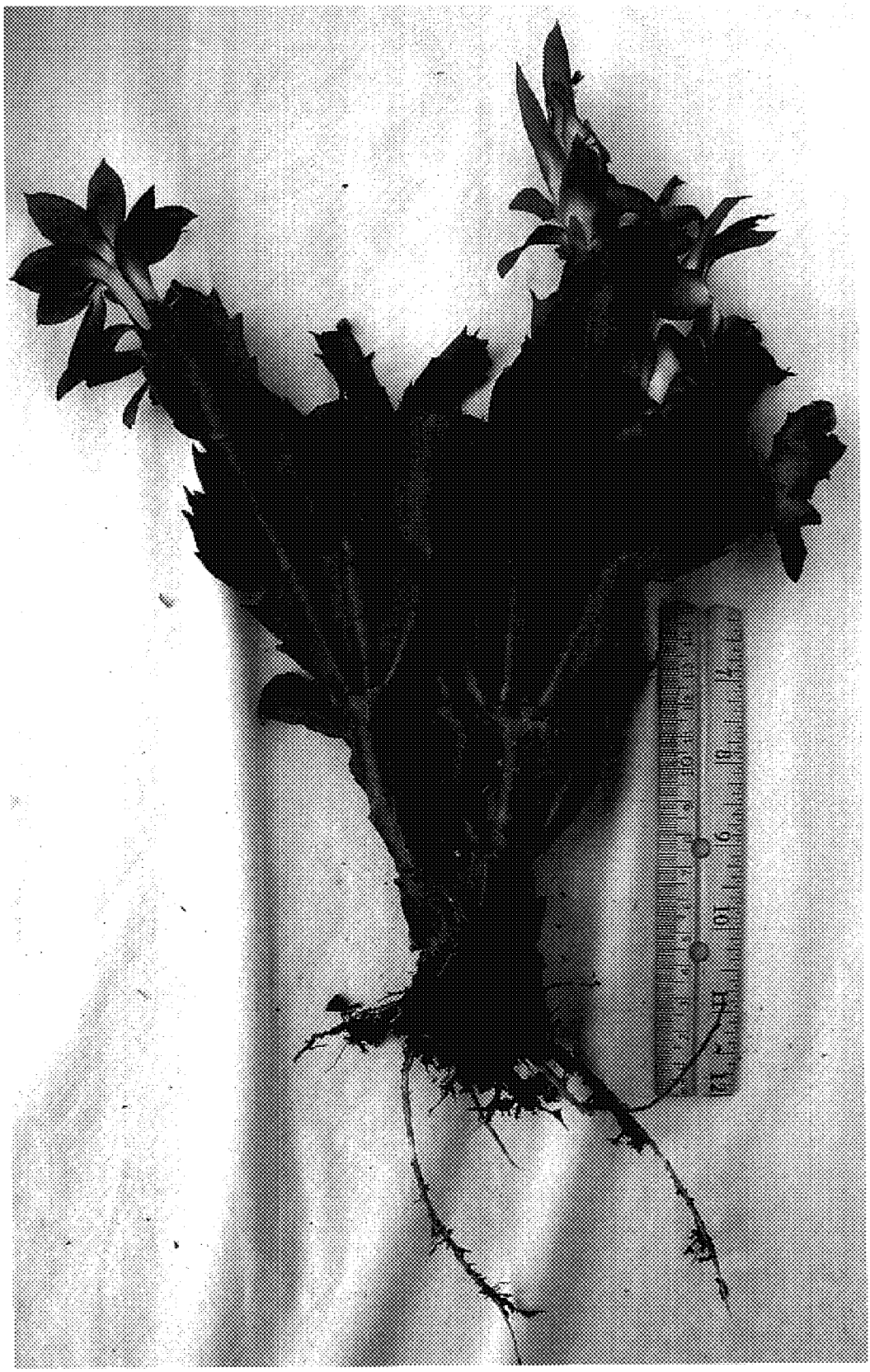
FIG. 12 is a color photograph of a single plant removed from its soil that grew from a single phylloclade cutting.
Figure 13:
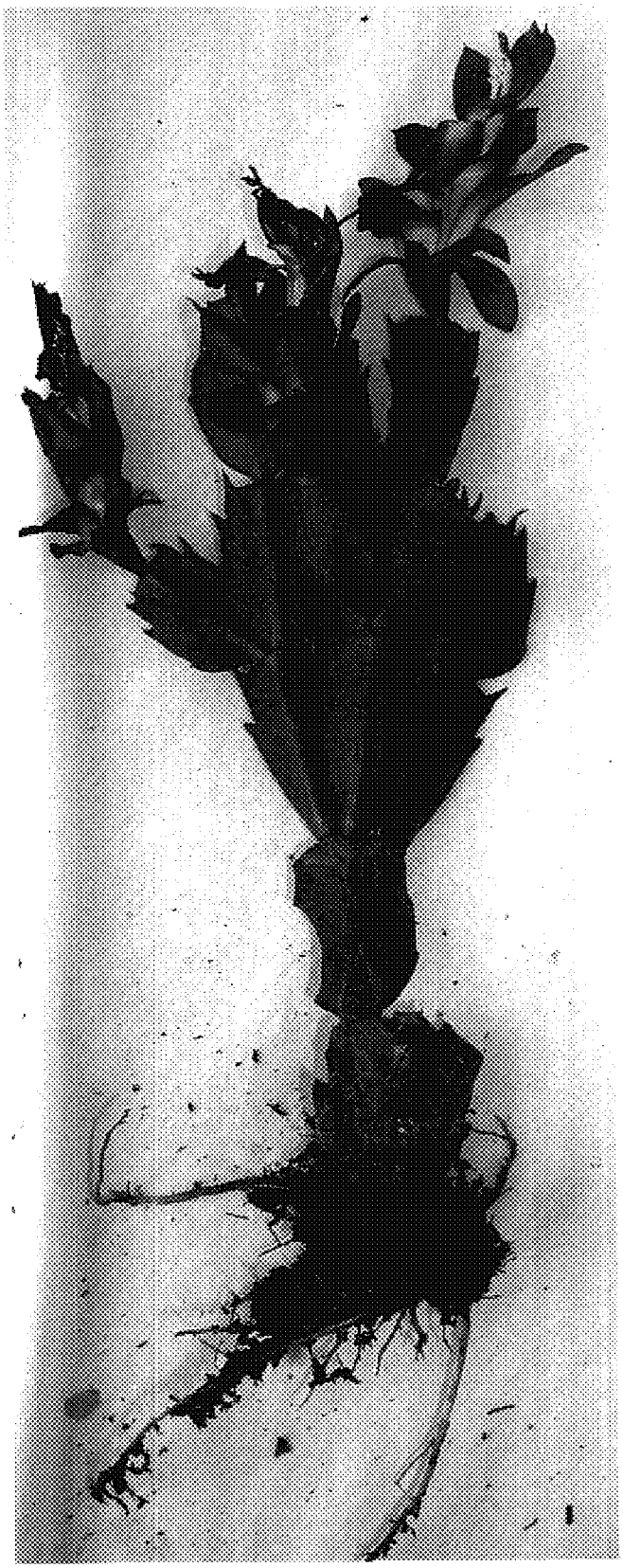
FIG. 13 is a color photograph of a single plant removed from its soil, and with many of its branches removed, that was propagated from a single phylloclade cutting.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Color Chart published by The Royal Horticultural Society of London, England.

The plants observed were grown in 6 inch pots. The tops of the plants observed were approximately 22 to 28 cm above the soil level. The following description is based on observations of optimally fertilized plants grown at a nursery in Half Moon Bay, Calif. The plants were mature. The plants were approximately 14 months old. Temperatures in Half Moon Bay on average range from 55 to 65 degrees Fahrenheit in the summer months, and from 45 to 55 degrees Fahrenheit in the winter months.

DETAILED PLANT DESCRIPTION

Name: *Schlumbergera truncata* 'Harmony'.

Classification:

*Family.*—Cactaceae.

*Tribe.*—*Cereus* (*Cacteae*).

*Genus.*—*Schlumbergera.*

*Species.*—*Schlumbergera truncate* (Haw.) Moran [*Epiphyllum truncatum* Haw.; *Zygocactus truncates* (Haw.) K. Schum.]. Bailey and Bailey and the staff of the Bailey Hortorium, *Hortus Third* (1976).

*Commercial.*—Thanksgiving Cactus, Christmas Cactus.

Form: Epiphytic, shade-loving, succulent, leafless plant with jointed and branched stems.

Stems:

*General.*—Irregular with much branching (especially when pinched) of upright, adventitiously rootable, flattened phylloclades that have a prominent midrib (especially in phylloclades at the base of mature plants) and prominently toothed lateral wings. Branching can be encouraged in the plant by pinching the top phyllocade.

*Phylloclades.*—General: The phylloclades are obovate to oblong, elongated and flattened (particularly when young) and have a transversely elongated, aerole bearing, truncated apex. From the transversely elongated apex, the wing margins generally run straight or taper slightly to the basal portions (or occasionally they flare outwardly somewhat, where they then taper and merge through a pointed, basal juncture with the phylloclade therebelow. The margins are also toothed and an axillary aerole is associated with each tooth. Size: Length — Mature phylloclades that are over a year old are usually between 45 mm and 53 mm. Width — Mature phylloclades that are over a year old are usually 25 mm to 35 mm. Thickness — Basal phylloclades with up to three levels of phylloclades above them can be as thick as 1 cm at the midrib. Young phylloclades are as thick as 3 to 4 mm at the center, and tapering to 1 mm near the edges. Color: Mature phylloclades are predominantly R.H.S. 147 A (yellow-green group), while young phylloclades are predominantly R.H.S. 146 A (yellow-green group). Midrib: General — Extends longitudinally of phylloclade and continuously through joints with laterally tapering cortex at wing insections. Pith surrounds the vascular bundles that branch and provide lateral extensions of the vascular system to marginal teeth. Texture — Smooth, waxy epidermis with wax in small embedded scales and becoming corky in basal stem areas with age. Wings: General shape — Generally flattened from midrib cortex to tooth insertions with slight thinning taper toward margins. Margins — Toothed (modified leaves). Texture — Succulent to leathery with smooth, waxy epidermis having wax arranged in small embedded scales and becoming corky in basal plant areas with age.

*Teeth.*—General shape — Generally flattened and tapering along margins from wing insertion to an apex, having a hyaline, pointed spine with nonpredicatable bending. Adaxial margin shape: Generally concave, so that teeth project generally distally of the phylloclade base in an alternate arrangement, but also with both straight and convex adaxial margin tendencies. Abaxial margin shape: Irregular with tendencies toward straight to convex. Tooth Margins: Entire. Texture — Succulent to leathery with a smooth waxy epidermis having wax in small embedded scales and becoming corky in basal plant areas with age. Number — Usually 3 to 4 on each side. Size — Teeth of mature phylloclades are 1 mm thick at insertion point with wings. Areole to apex dimension (adaxial margin side): usually 3 to 8 mm in length.

*Areoles.*—Terminal areole — Large, compound, elongated, oval-shaped with several acicular bristles, copious multi-cellular hairs, and several buds that may mature into either new phylloclades or flowers. The opposite ends of the areole are located adjacent to subsidiary areoles which are in turn located at the axils of the uppermost teeth located at the distal end of the of phylloclade. Axillary aeroles — Acicular bristles without glochidia but having copious, short, R.H.S 199D (grey-brown group), to colorless, multicellular hairs. Areoles are sometimes found in the basal portion of the phylloclade in association with a vestigial tooth that is less than 1 mm in length (Vestigial teeth not considered in teeth number or length of teeth.)

Buds: Unarmored and ovoid, without spines or barbs, generally R.H.S. 74B (red — purple group)). Buds grow quickly into flowers. When they first become apparent they are typically 1 mm wide by 1 mm long.

Flowers:

*General.*—Sessile, zygomorphic, usually in pairs, triplets or solitary, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals. Plants typically bloom once a year in the winter and are easily forced to bloom with the blooming period lasting three weeks and individual flowers blooming for about two weeks.

*Sepaloid series of tepals.*—General: Free tepals inserted on top of the ovary. Shape: Deltoid in outer members of the whorl and grading inwardly on the whorl to tepals which are ovate and less frequently elliptical. Tips are broadly acuminate with some acute tendencies, and margins are entire with sparse irregular teeth appearing mainly in the apex areas. Texture: Succulent and glabrous outer whorl members and grading inwardly in the whorl to silken blades with fleshy basal areas. Number: Usually 7 to 9. Size (at full bloom): Base-tip dimension — 5 mm to 26 mm. Width dimension — 5 mm to 14 mm. Color: The sepaloid series of tepals are predominantly R.H.S. 53 A (red group) with only small basal portions lacking pigment, if at all. The interface between pigmented upper portion and the non-pigmented lower portion, and the attachment interface to the ovary can be R.H.S. 74 A (red-purple group). The outermost and smallest tepals can have R.H.S. 147 B (yellow-green group) bases. The outermost and smallest tepals can also tend toward R.H.S. 74 A (red-purple group).

*Tube laminating series of tepals.*—General: Tepals inserted on ovary and basally united below the throat as outer laminations on the perianth tube and with progressively greater amounts of basal fusion inwardly in the whorl. Shape: Grading inwardly in the whorl with progressively longer base-tip dimensions and with blade areas changing inwardly from ovate to broadly elliptical and with acute tips. Entire margins with sparse irregular teeth mainly in apex areas. Texture: Succulent, slightly fleshly basal areas with silken blades. Number: 6 to 11. Size (at full bloom): Base-tip dimensions — 35 mm to 55 mm. Width dimension — 15 and 20 mm. Color: The margins and distal ends of the tube laminating series of sepals are R.H.S. 46 B (red group) on both the abaxial and adaxial surfaces. The central, basal portions of these tepals lack pigment. The attachment interface to the tube can be R.H.S. 74 A (red-purple group).

*Tube forming series of tepals.*—General: Tepals basally united to form a hollow perianth tube that is inserted on ovary and equipped with a irregular carina (keel) at the throat. Shape: Perianth tube — Elongated and ellipsoidal to oval in cross-section. Blades — Generally elliptic to broadly elliptic with ovate tendencies and with acuminate tips. Entire margins with sparse, irregular teeth mainly in apex area. Carina (keel) — Transcending and irregular. Texture: Perianth tube — Thick, succulent, and slightly ribbed. Blades — Translucent and silken. Carina (keel) — Fleshy. Blade number: 5 to 8. Size (at full bloom): Base-tip dimension — 50 mm to 70 mm. Perianth tube — Base to throat length is 35 to 45 mm. Typical perianth tube diameter is 8 mm. Color (at full bloom): Perianth tube — R.H.S. 68 D (red-purple group). Blades — Margins and much of the blades at maturity are R.H.S. 46 B (red group). The inner interface between the blades of the tube forming tepals and the tube is R.H.S. 74 A (red-purple group). The central portions of the blades just above the tube are R.H.S. 155 C (white group). Orientation at full bloom: The blades of tube forming tepals are reflexed, the tube is angled from the axis of the ovary.

*Androecium* (*stamens*).—General: Numerous exerted and diadelphous stamens with one group having filaments basally fused to the perianth tube and the other group having filaments basally united to form a nectary housing. Filament: General — Translucent and glabrous with anther connective. Shape — Long, slender and gradually tapering from base to anther connective. Texture — Glabrous and silken. Color — Translucent white R.H.S. 155D (white group). Number — approximately 80. Size (at full bloom) — Length: 40 mm to 65 mm. Anthers: Shape — Rod shaped. Size — 1 mm long. Texture — Course or grainy. Color (pollen color) — R.H.S. 10 C (yellow group).

*Gynoecium* (*pistil*).—General: Compound, parietal placentation with united style surrounded by an annular diffuse nectary at its insertion. Style: General — Stout and inserted in ovary. Shape — Elongated. Texture — Fleshy and glabrous. Color — R.H.S. 46 B (red group) just below stigma, changing to 71 B (red-purple group) at its base. Size (at full bloom) — 65 mm long. Stigma: General — Exserted and erect with anywhere from 4 to 7 inner marginally adhering lobes. Shape — Elongated and tapering toward lobe tips and having relatively blunt apices. Texture — Fleshy and smooth with short glutinous hairs. Color — R.H.S. 74 A (red-purple group). Size — 4 mm long. Ovary: General — Thin epidermis and distally located concavity, and with a single cavity usually having 6 or 7 carpels with numerous ovules. Shape — Terete to ovoid and generally broadening from insertion to floral end. Texture — Succulent and glabrous with thin outer epidermis.

*Fruit.*—Generally flowers wither and become desiccated along with the ovary and together they fall of the plant without having produced fruit.

I claim:

1. A new and distinct variety of Cactaceae plant, substantially as herein shown and described.

* * * * *